US005527776A

United States Patent [19]
Carlino et al.

[11] Patent Number: 5,527,776
[45] Date of Patent: Jun. 18, 1996

[54] TREATMENT OF IMMUNOLOGIC AND HEMATOLOGIC DISORDERS WITH IGFBP ALONE OR COMPLEXED WITH IGF

[75] Inventors: Joseph A. Carlino, San Leandro; Howard R. Higley, Mountain View; Christopher A. Maack, El Cerrito, all of Calif.

[73] Assignee: Celtrix Pharmaceuticals

[21] Appl. No.: 393,249

[22] Filed: Feb. 23, 1995

Related U.S. Application Data

[63] Continuation of Ser. No. 124,410, Sep. 20, 1993, abandoned.
[51] Int. Cl.$^6$ .............................. C07K 2/00; C07K 14/00; A61K 38/27
[52] U.S. Cl. ......................... 514/12; 530/324; 530/350; 530/399
[58] Field of Search .................................... 530/324, 350, 530/399; 514/12

[56] References Cited

U.S. PATENT DOCUMENTS

| | | | |
|---|---|---|---|
| 4,876,242 | 10/1989 | Applebaum et al. | 514/3 |
| 5,187,151 | 2/1993 | Clark et al. | 514/3 |
| 5,202,119 | 4/1993 | Clark et al. | 424/88 |

FOREIGN PATENT DOCUMENTS

| | | |
|---|---|---|
| WO89/05822 | 6/1989 | Australia. |
| 0128733 | 12/1984 | European Pat. Off.. |
| WO92/13556 | 8/1992 | WIPO. |
| WO93/00110 | 1/1993 | WIPO. |

OTHER PUBLICATIONS

Blum et al., "Plasma IGFBP-3 levels as clinical indicators" *Modern Concepts in Insulin–like Growth Factors* (1991) Spencer, E. M., ed., Elsevier Publishers, New York pp. 381–393.

Rinderknecht et al., "Polypeptides with nonsuppressible insulin–like and cell–growth promoting activities in human serum: Isolation, chemical characterization, and some biological properties of forms I and II" *Proc. Natl. Acad. Sci. USA* (1976) 73:2365–2369.

Baxter et al., "Growth hormone–dependent insulin–like growth factor (IGF) binding protein from human plasma differs from other human IGF binding proteins" *Biochem. Biophys. Res. Commun.* (1986) 139:1256–1261.

Sommer et al., "Molecular genetics and actions of recombinant insulin–like growth factor binding protein—3" *Modern Concepts in Insulin–like Growth Factors* (1991) Spencer, E. M., ed., Elsevier Publishers, New York, pp. 715–728.

Skottner et al., "Anabolic and tissue repair functions of recombinant insulin–like growth factor I" *Acta Paediatr. Scand.* (1990) 367:63–66.

Gala, "Prolactin and growth hormone in the regulation of the immune system" *PSEBM* (1991) 198:513–527.

Murphy et al., "Immunologic and hematologic effects of neuroendocrine hormones" *J. Immunol.* (1992) 148:3799–3805.

Binz et al., "Repopulation of the atrophied thymus in diabetic rats by insulin–like growth factor I" *Proc. Natl. Acad. Sci. USA* (1990) 87:3690–3694.

Hodgkinson et al., "Distribution of circulating insulin–like growth factor I (IGF–I)" into tissues *Endocrinology* (1991) 129(4):2085–2093.

Beschocmer et al., "Enhancement of thymic recovery after cyclosporine by recombinant human growth hormone and insulin–like growth factor I" *Transplantation* (1991) 52(2):879–884.

Aron et al., "Insulin–like growth factor I and erythropoiesis" *BioFactors* (1992) 3(4):211–216.

Quaife et al., "Histopathology associated with elevated levels of growth hormone and insulin–like growth factor I in transgenic mice" *Endocrinology* (1989) 124(1):40–48.

Intebi et al., "Active B–Cell differentiation under PWM induction acromegaly" *Prog. Neuroendoimmunol.* (1992) 5(1):62–69.

Jennische et al., "Dynamic changes in insulin–like growth factor I immunoreactivity correlate to repair events in rat ear after freeze–thaw injury" *Exp. Mol. Pathol.* (1987) 47:193–201.

Spencer et al., "Somatomedins: Do they play a pivotal role in wound healing?" *Growth Factors and Other Aspects of Wound Healing: Biological and Clinical Implications* (1988) Alan R. Liss Publishers, pp. 103–116.

Baxter et al., "Characterization of immunoreactive insulin––like growth factor–I from leukocytes and its regulation by growth hormone" *Endocrinol.* (1991) 129(4):1727–1734.

Stuart et al., "Insulin–like growth factor–I binds selectively to human peripheral blood monocytes and B–lymphocytes" *J. Clin. Endocrinol. Metab.* (1991) 72(5):1117–1122.

Kooijman et al., "Expression of type I insulin–like growth factor receptors on human peripheral blood mononuclear cells" *Endocrinol.* (1992) 131:2244–2250.

Marchav et al., "Enhancement of human granulopoiesis in vitro by biosynthetic insulin–like growth factor I/sometomedin C and human growth hormone" *J. Clin. Invest.* (1988) 81:791–797.

(List continued on next page.)

*Primary Examiner*—Howard E. Schain
*Assistant Examiner*—Lynn Touzeau
*Attorney, Agent, or Firm*—Morrison & Foerster

[57] ABSTRACT

This invention includes a method of treating subjects with immunologic and hematologic disorders, such as immune deficiencies and anemias characterized by deficient total hemoglobin. The treatment includes administering to the subject insulin-like growth factor binding protein-3 (IGFBP-3), alone or in a complex including an insulin-like growth factor (IGF), in an amount sufficient to improve the immunologic and/or hematologic disorder, for example, increasing the level of total hemoglobin or improving immune deficiencies, such as occur post-chemotherapy. Another aspect of the invention includes administering IGFBP-3 alone to treat IGF-driven lymphoproliferative conditions, such as leukemias, inflammatory skin diseases, and nasal polyps.

1 Claim, 3 Drawing Sheets

OTHER PUBLICATIONS

Zapf et al., "In vivo models of IGF binding protein (IGFBP) regulation with possible relevance to their physiological roles" *Modern Concepts in Insulin–like Growth Factors (1991) Spencer, E. M., ed., Elsevier Publishers, New York, pp. 591–605.*

Kooijman et al., "Effects of insulin–like growth factors and growth hormone on the in vitro proliferation of T lymphocytes" *J. Neuroimmunol.* (1992) 38:95–104.

Neely et al., "Mitogenic effects of human recombinant insulin on B-cell precursor acute lymphoblastic leukemia cells" *Leukemia* (1992) 6(11):1134–1142.

Krane et al., "Insulin–like growth factor–I (IGF–I) receptor expression may regulate keratinocyte proliferative potential in normal and psoriatic epidermis" *J. Invest. Dermatol.* (1991) 96(4):544A (abstract No. 71).

Geffner et al., "Growth hormone mediates the growth of T–lymphoblast cell lines via locally generated insulin–like growth factor–I" *J. Clin. Endocrinol.* (1990) 71(2):464–469.

Liu et al., "Insulin–like growth factor binding protein (IGFBP-3), an inhibitor of serum growth factors other than IGF–I and –II" *J. Cell. Physiol.* (1992) 153:15–21.

Cohen et al., "Transfection of the human insulin–like growth factor binding protein-3 gene into Balb/c fibroblasts inhibits cellular growth" *Mol. Endocrinol.* (1993) 7:380–386.

Barak et al., "Enhanced response of human circulating erythroid progenitor cells to hGH and to IGF–I in children with insufficient growth hormone secretion" *Pediatric Res.* (1992) 32(3):282–285.

Boyer et al., "Roles of erythropoietin, insulin–like growth factor I, and unidentified serum factors in promoting maturation of purified murine erythroid colony–forming units" *Blood* (1992) 80(10):2503–2512.

Bozzola et al., "Immunological and endocrinological response to growth hormone therapy in short children" *Acta Pediatr. Scand.* (1988) 77:675–680.

Chatelain et al., "Paracraine and autocrine regulation of insulin–like growth factor I" *Acta Pediatr. Scand.* (1991) 372:92–95.

Fu et al., "A novel role of growth hormone and insulin–like growth factor–I" *J. Immunol.* (1991) 146(5):1602–1608.

Huang et al., "Formation of haematopoietic microenvironment and haematopoietic stem cells from single human bone marrow stem cells" *Nature* (1992) 360:745–749.

Landreth et al., "Insulin–like growth factor–I regulates Pro–B cell differentiation" *Blood* (1992) 80(5):1207–1212.

Merchav et al., "Comparative studies of the erythroid–potentiating effects of biosynthetic human insulin–like growth factors–I and II" *J. Clin. Endocrinol. Metab.* (1992) 74(2):447–451.

Miller et al., "Alterations of erythropoiesis in TGF–β1–treated mice" *Exp. Hematol.* (1992) 20:951–956.

Urena et al., "Insulin–like growth factor I: A Moderator of erythropoiesis in uraemic patients?" *Nephrol. Dial. Transplant.* (1992) 7:40–44.

Baxter, *Comp. Biochem. Physiol.* vol. 91B, No. 2, 229–235, 1991.

*Bioventure View*, vol. IV, No. 1, 19–24, 1989.

Werther et al., "Insulin–like growth factors promote DNA synthesis and support cell viability in fetal hemopoietic tissue by paracrine mechanisms" *Growth Factors* (1990) 3:171–179.

TREATMENT OF IMMUNOLOGIC AND HEMATOLOGIC DISORDERS WITH IGFBP ALONE OR COMPLEXED WITH IGF

This application is a continuation of application Ser. No. 08/124,410, filed Sep. 20, 1993 now abandoned.

DESCRIPTION

1. Technical Field

This invention relates to the treatment of immunologic and hematologic diseases. The method comprises administering insulin-like growth factor binding protein IGFBP either alone or in a complex with insulin-like growth factor (IGF).

2. Background Art

Growth factors are polypeptides which stimulate a wide variety of biological responses (e.g., DNA synthesis, cell division, expression of specific genes, etc.) in a defined population of target cells. A variety of growth factors have been identified including transforming growth factor-β1 (TGF-β1), TGF-β2, TGF-β3, epidermal growth factor (EGF), platelet-derived growth factor (PDGF), fibroblast growth factor (FGF), insulin-like growth factor-I (IGF-I), and IGF-II.

IGF-I and IGF-II are polypeptides related in sequence and structure, with each molecule having a molecular weight of approximately 7500 daltons. IGF-I acts as the mediator of the effects of growth hormone and thus is the primary mediator of growth after birth. IGF-I has also been implicated in the actions of various other growth factors, since treatment of cells with such growth factors leads to increased production of IGF-I. Both IGF-I and IGF-II have insulin-like activities (hence the name), and are mitogenic for the cells in reproductive tissue, muscle, skeletal tissue and a wide variety of other tissues.

Unlike most growth factors, the IGFs are present in substantial quantity in the circulation, but only a very small fraction of this IGF is found in the free form in the circulation or in other body fluids. The overwhelming majority of IGF circulates as part of a non-covalently associated ternary complex composed of IGF-I or IGF-II, an IGF specific binding protein termed IGFBP-3, and a large protein termed the acid labile subunit (ALS). This complex is composed of equimolar amounts of each of the three components. The ALS has no direct IGF binding activity and is thought only be able to bind a preformed IGF-I/IGFBP-3 complete, The ternary complex of IGF+IGFBP-3+ALS has a molecular weight of approximately 150,000 daltons, and it has been suggested that the function of such a unit in the circulation "may be regarded as a reservoir and a buffer for IGF-I and IGF-II preventing rapid changes of free IGF." See Blum, W. F., et al. (1991), "Plasma IGFBP-3 levels as clinical indicators," in *Modern Concepts in Insulin-Like Growth Factors* (E. M. Spencer, ed., Elsevier, N.Y., pages 381–393.

Nearly all of the IGF-I or IGF-II and IGFBP-3 in the circulation are complexed with each other, so there is very little free IGF or IGFBP-3 detectable. High levels of free IGF in plasma must be avoided as they would lead to serious hypoglycemia due to IGF's insulin-like effects on glucose transport into tissues. In contrast to the IGFs and IGFBP-3, there is a substantial pool of free ALS present in plasma which is available for ternary complex formation with exogenously administered IGF-I/IGFBP-3 complex.

Although IGFBP-3 is the most abundant IGF binding protein in the circulation, at least five other distinct IGF binding proteins (IGFBPs) have been identified in various tissues and body fluids. Although these proteins bind IGFs, they each have distinct amino acid sequences, and are not merely processed forms of a common precursor. Unlike IGFBP-3, the other IGFBPs that are present in the circulation are not saturated with IGFs and constitute the majority of the available soluble IGF binding sites in plasma. None of the IGF binding proteins other than IGFBP-3 can form the 150 kd circulating ternary complex.

IGF-I and IGFBP-3 may be purified from natural sources or produced from recombinant sources. For instance, IGF-I has been purified from human serum for a number of years. See, Rinderknecht, E. W., et al. (1976), *Proc. Natl. Acad. Sci.* (USA) 73: 2365–2369. Recombinant IGF-I processes are shown in EPA 0,128,733, published in December 1984. IGFBP-3 may be purified from natural sources using processes such as those shown in Baxter et al. (1986), *Biochem. Biophys. Res. Comm.* 1.39:1256–1261. It may be synthetically produced from recombinant sources as discussed in Sommer, A. S., et. al. (1991), in *Modern Concepts of Insulin-Like Growth Factors* (E. M. Spencer, ed., Elsevier, N.Y.), pages 715–728.

IGF-I may be measured in blood serum to diagnose abnormal growth-related conditions, e.g. pituitary gigantism, acromegaly, dwarfism, various growth hormone deficiencies, etc. Although IGF-I is produced in many tissues, most circulating IGF-I is believed to be synthesized in the liver.

Many of the important elements of the IGF system are found in the immune and hematopoietic systems of higher organisms. These tissues produce both formed cellular elements and soluble proteins within the circulatory system that transport oxygen, promote hemostasis and defend against foreign pathogens. The development and differentiation of white blood cells, red blood cells, platelets, immunoglobulins and complement in the typical mammal are complex and involve diverse organ systems and signaling molecules.

In the adult mammal the primary site of hematopoiesis is the bone marrow. Maturation and differentiation of specialized subsets of blood cells takes place in the thymus, spleen, lymph nodes and gut-associated lymphoid tissues. Production and integration of function of the immune and hematopoietic systems are coordinated not only by the protein and steroid hormones, but also by multiple classes of short-range paracrine growth factors. These include the interleukins and hematopoietins as well as several neuroendocrine-like substances. Insulin-like growth factor-one (IGF-I) specifically regulates the cells and tissues of the immune and hematopoietic systems in health and disease. These effects occur in addition to the well recognized influence of IGF-I on general metabolic growth control.

Disequilibrium of the pituitary/endocrine axis impacts immune function. Hypophysectomy, dwarfism and diabetes immunosuppress rodents with accompanying lymphoid organ involution. Skottner, et al. (1990), *Acta Paediatr. Scand.* (Suppl), 367:63–66; Gala, R. (1991), *PSEBM*, 198:513–527; Murphy, W., et al., (1992), *J. Immunol.* 148:3799–3805; and Binz, K., et al. (1990), *PNAS*, 87:3690–3694. IGF-I, as the primary modulator of growth hormone's (GH) general anabolic action, may be insufficiently available in these endocrine immunodeficiency states. Gala et al. and Binz et al. further show that replacement therapy with either GH or IGF-I partially restores, variously, T-cell proliferation, allograft reactivity and immunoglobulin production by B-cells to normal levels. The fact that infused IGF-I distributes predominantly to the spleen and kidney Hodgkinson, S., et al. (1991), *Endocrinology* 129(4):2085–2093), indicates that lymphoid tissue may be a prominent site of IGF utilization.

Other immunodeficiency states not due to endocrine disturbance may also respond to IGF-I administration. After cyclosporin treatment causes thymic involution, and loss of T-cell and antigen presenting cell function, IGF treatment can reverse the effects. Beschorner, W., et al. (1991), *Transplantation* 52(5):879–884.

IGF-I also modulates red cell mass. Aron, D. (1992), *BioFactors* 3(4):211–216. Administration of IGF-I to hypophysectomized rats increases the level of erythropoietin in the blood independently of any change in hematocrit. Kurtz, A., et al. (1988), *PNAS* 85:7825–7829. In transgenic mice which overexpress either GH or IGF-I, the spleen is congested and red cell production increases. Quaife, C., et al. (1989), *Endocrinology* 124(1):40–48. In contrast, in acromegalic patients (with an excess of GH), there is no obvious increase of red blood cells and immune function is considered generally normal or even slightly deficient. Intebi, A., et al. (1992), *Prog. NeuroEndoImmunol.* 5(1):62–69.

In addition to IGF's systemic effects on metabolism and immunity, local IGF production is an important feature of cell-cell signaling in repair and differentiation in several organs, including those of the immune and hematopoietic systems. Jennische, E., et al. (1987), *Exp. Mol. Pathol.* 47:193–201; Spencer, E., et al. (1988) "Somatomedins: Do they play a pivotal role in wound healing?" In *Growth Factors and Other Aspects of Wound Healing: Biological and Clinical Implications,* Alan Liss. Pages 103–116.

Baxter et al. and Stuart et al. have found IGF receptors on lymphoid cell lines, macrophages, B-cells and erythroid cells and also found that normal human peripheral blood leukocytes can secrete immunoreactive IGF-I in vitro. Baxter, J., et al. (1991), *Endocrinology* 129(4):1727–1734, and Stuart, C., et al. (1991), *J. Clin. Endocrinol. Metab.* 72(5):1117–1122. This "lymphoid tissue" IGF-I is chemotactic for lymphocytes and monocytes and stimulates bacteriocidal superoxide production by neutrophils. Kooijman, R., et al. (1992), *Endocrinology* 2244–2250. IGF-I also enhances myeloid differentiation, increasing the numbers of granulocyte precursors in vitro. Marchav, et al. (1988) *J. Clin. Invest.* 81:791–97.

As described by Zapf et al. In: *Modern Concepts of Insulin-Like Growth Factors* (Ed. by Spencer) pp. 583–90, supra, IGF-I directly mediates general anabolic effects and specific immunostimulatory actions, although IGF-I is not found free in the circulation in substantial amounts but rather is bound to several distinct binding proteins. The levels of IGFBP-3, the major protein carrier, and its mRNA in lymphoid tissue are second only to those in the "major" site of synthesis, the liver. Naya, F., et al. (1991). IGF-I-augmented lectin-driven T-cell proliferation can be inhibited by the in vitro addition of IGF binding proteins, suggesting that these natural IGF modulators may down regulate the immune response, Kooijman, R., et al. (1992), *J. Neuroimmunol.* 38:95–104.

Some pathologic inflammatory or hematopoietic conditions may be attributable to IGF-I hypersecretion and/or binding protein deficiency. These disorders include leukemias and lymphomas that may respond to IGF-I or insulin with increased proliferation, or inflammatory skin diseases such as psoriasis in which excessive IGF-I levels have been noted. Neely, E., et al., (1992), *Leukemia* 6(11):1134–1142; and Krane, J., et al. *J. Invest. Dematol.* 96(4):544A.

Therefore, there is a need in the art to regulate the immune response or hematopoiesis via administration of components of the IGF system.

In a series of experiments, Clark and Jardieu (U.S. Pat. No. 5,202,119) administered IGF alone or with growth hormone. They describe the specific immunostimulatory effects of IGF-I alone, IGF+growth hormone and des(1–3)-IGF. IGF was administered via an osmotic mini-pump to avoid the well known hypoglycemic effects of bolus injection of IGF-I. These workers propose coadministration of IGF-I with binding proteins, including glycosylated IGFBP-3, but report no results therewith.

In U.S. Pat. No. 5,187,151, Clark and Mukku observed, along with the general anabolic effect of IGF-I complexed with IGFBP-3, an increase in select lymphoid organ weights. Clark and Mukku disclosed no effect on specific immune or hematopoietic organ function. There is no indication whether these organ weight changes could effect an increase in active leukocytes in these organs or in the periphery. There are no suggestions of specific hematopoietic disorders that might benefit from IGF-I/IGFBP-3 therapy.

In U.S. Pat. No. 4,876,242, Applebaum et al. describe IGF analogs designed to avoid serum binding proteins and to be more active than IGF. Applebaum et al. propose using the analogs when endogenous IGF levels are low and to stimulate erythropoiesis, but no data on erythropoietic effects are given.

Finally, while local application of supraphysiologic doses of the IGF-I binding protein IGFBP-3 alone has been described as a method of reducing endogenous IGF-I driven connective tissue production in an animal model of excessive wound repair (Sommer et al. (1991), supra), it has not been proposed to use the binding protein as an antagonist for the treatment of IGF-I-dependent immunopathies. Although IGF-I antagonists such as antibodies to IGF-I have been shown to inhibit IGF function in vitro, treatment with the natural "nonimmunogenic" binding proteins may also be a practical method to intervene therapeutically in inflammatory, neoplastic or autoimmune diseases. Gefner et al. (1990), *J. Clin. Endocrinol. Metab.* 71(2):464–469. Demonstrations of the binding protein's ability to antagonize cellular functions in vitro have thus far been conducted on a variety of cell lines. Liu, L., et al. (1992), *J. Cell. Physiol.* 153:15–21; Cohen, P., et al., (1993), *Mol. Endrocrinol.* 7:380–386.

DISCLOSURE OF THE INVENTION

In view of this art, the present invention represents an unexpected finding that the IGF-I/IGFBP-3 complex can be used to treat anemias in a subject with deficient total hemoglobin.

In another embodiment, there is provided a treatment for subjects with IGF-driven lymphoproliferative conditions. Those conditions are treated by administering to a subject insulin-like growth factor binding protein-3 (IGFBP-3) in an amount sufficient to slow the progression of the IGF-driven lymphoproliferative condition. These lymphoproliferative conditions include, but are not limited to, leukemias, inflammatory skin and gastrointestinal diseases and nasal polyps.

While not wishing to be bound by any particular theory, the inventors propose that the administered complex of IGF and IGFBP-3 results in the gradual release of free IGF in somewhat elevated levels. This can occur either before or after the circulating IGF/IGFBP-3 complex is taken up into the lymphoid tissue. Treatment with the IGF-I/IGFBP-3 complex can increase lymphoid and hematopoietic organ mass and potentiate or stimulate the immune response and blood cell production.

In addition, while not wishing to be bound by any particular theory, the inventors also propose that administration of IGFBP-3 alone can result in the binding and neutralization of excess IGF-I that is driving the pathologic proliferation of hematogenous tumors or inflammatory diseases and thereby reduce, arrest or reverse the progression of these disorders.

MODE FOR CARRYING OUT THE INVENTION

Definitions

Figure 1:
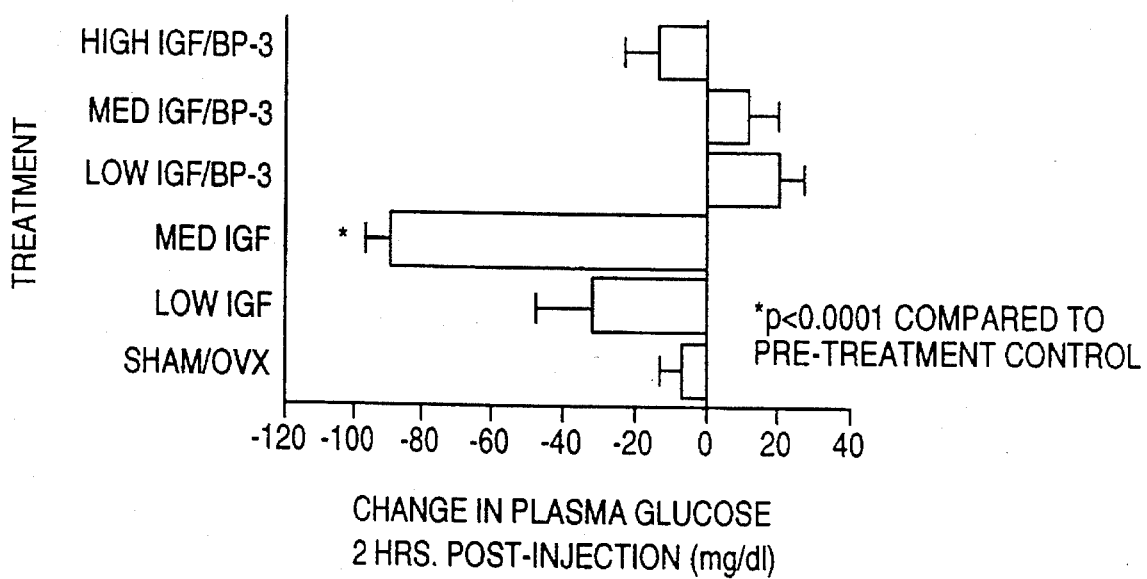
FIG. 1 graphically presents plasma glucose levels two hours post-injection.

Anemias characterized by deficient total hemoglobin level are intended to be treated by the inventive method. A deficient total hemoglobin is below about 13 g/dL in adult men and below about 12 g/dL in adult women. An example of such an anemia is that associated with renal insufficiency and hemodialysis.

As used herein, "immune system disorders" are defined as previous treatment with chemotherapeutic agents, radiation, immunosuppressive and anti-inflammatory drugs and dialysis; conditions such as severe combined immunodeficiency, congenital thymic aplasia, aplastic anemia, viral infections, chronic granulomatous disease and immune dysfunction associated with diabetes; adverse reactions to bone marrow or organ transplantation such as graft-versus-host disease; physical findings such as rashes, fevers, and those indicative of leukemias, lymphomas, inflammatory bowel disease or psoriasis. Immune systemic disorders also include allergic conditions such as nasal polyps.

"Subjects" are defined as humans and mammalian farm animals, sport animals and pets. Farm animals include, but are not limited to, cows, hogs and sheep. Sport animals include, but are not limited to, dogs and horses. The category pets includes, but is not limited to, cats and dogs.

"Insulin-like growth factor (IGF)" comprises a family of factors, including but not limited to IGF-I and IGF-II. IGF is a polypeptide having a molecular weight of about 7500 daltons. IGF may be obtained from natural sources or prepared by recombinant means.

"Insulin-like growth factor binding proteins (IGFBP)" comprises a family of binding proteins, including but not limited to IGFBP-1, IGFBP-2, IGFBP-3, IGFBP-4, IGFBP-5 and IGFBP-6. IGFBP may be obtained from natural sources or prepared by recombinant means. At least one form of IGFBP (for example, IGFBP-3) complexes with IGF and with a third molecule known as ALS.

A "therapeutic composition" as used herein is defined as comprising IGF complexed with its binding protein IGFBP-3. However, for treating conditions of IGF excess, a "therapeutic composition" is defined as IGFBP-3 alone. These therapeutic compositions may also contain excipients such as water, minerals and carriers such as proteins.

DESCRIPTION OF THE INVENTION

The method of the present invention contemplates treating and alleviating conditions in subjects suffering from immunosuppression, anemias and bone marrow aplasias by administering a complex of IGF and IGFBP-3.

Nearly all IGF-I or IGF-II is bound to IGFBP-3 and IGF/IGFBP-3 normally circulates in the form of a complex in humans and other mammals. This complex associates with a third protein (ALS), which is present in excess over the concentrations of IGF and IGFBP-3. Therefore, ALS is found both associated with the IGF/IGFBP-3 complex and in the free form. The resultant ternary complex has a size of about 150 kD. Administration of IGF and IGFBP-3, either from natural or recombinant sources, as a preformed complex results in the formation of the normal ternary complex with the excess ALS. This type of treatment appears to produce a long term increase in the level of circulating IGF, which is gradually released from the ternary complex. This mode of administration avoids the detrimental side effects associated with administration of free IGF-I, e.g., hypoglycemia, suppression of growth hormone and ALS production, and release of endogenous IGF-II since administered exogenous free IGF-I displaces endogenous IGF-II in normally circulating IGF-II/IGFBP-3/ALS complexes. Moreover, a greater total dosage of IGF-I can be safely delivered when complexed to its binding protein IGFBP-3 because of the protection provided by the complex from the generation of injurious hypoglycemia. Although this side effect of free IGF-I administration may be avoided in part by slow infusion or by multiple low dose treatments with IGF-I, treatment with the IGF-I/IGFBP-3 complex is more convenient, less expensive and more likely to meet with higher patient compliance.

IGF/IGFBP-3 treatment can increase lymphoid and hematopoietic organ mass, and potentiate/stimulate the immune response/blood cell production. This method can be useful in the treatment of subjects suffering from anemias with low hemoglobin, and including, but not limited to, immunosuppression, bone marrow aplasias resulting from such disorders and side effects of therapy as, severe combined immunodeficiency, congenital thymic aplasia, aplastic anemia, viral infections, chronic granulomatous disease, and the immune dysfunction associated with diabetes as well as leukopenias and anemias resulting from treatments with chemotherapeutic agents, radiation, immunosuppressive and anti-inflammatory drugs and dialysis.

Treatment with IGFBP-3 alone can neutralize or inactivate endogenous IGF-I and thereby reduce lymphoid organ weights. Thus, IGFBP-3 administrataion is useful in the treatment of disorders that result from physiologically excessive levels of IGF-1 that are driving pathologic proliferation of hematogenous tumors or inflammatory diseases.

Treatment with the binding protein, IGFBP-3 can thereby reduce, arrest or reverse the progression of these disorders, including leukemias, lymphomas, autoimmune and hyperproliferative conditions such as inflammatory bowel disease and psoriasis or adverse bone marrow transplantation reactions like graft-versus-host disease.

The formulation, method of administration and dosage will depend upon the disorder to be treated, and the medical history of the patient. These factors are readily determined in the course of therapy. Suitable patients with immunodeficiency or hematologic disorders can be identified by medical history, physical findings and laboratory tests. The medical history may reveal such facts as previous treatment with chemotherapeutic agents, radiation, immunosuppressive and anti-inflammatory drugs and kidney dialysis. Patients may have physical findings which are quite varied and include those associated with severe combined immunodeficiency, congenital thymic aplasia, aplastic anemia, viral infections, chronic granulomatous disease, immune dysfunction associated with diabetes and allergic conditions such as nasal polyps. Indicative laboratory results include decreased immunoglobulin levels, leukopenia, serum IGF-I levels (If low, the complex is indicated; if high, IGFBP-3 is useful) decreased platelet counts, inverted T helper/T suppressor ratio, decreased in vitro mixed lymphocyte reactions, mitogenicity assays and/or phagocyte function tests, impaired skin test response, decreased hematocrit, and abnormal reticulocyte levels.

In accordance with the method of the present invention, the formulation comprises a complex of IGF and IGFBP-3. Preferably, the IGF is IGF-I, although IGF-II may be useful. Because IGF and IGFBP-3 naturally complex in a 1:1 molar ratio, a composition of equimolar amounts of IGF and IGFBP-3 is preferred. The product can be formulated with IGF:IGFBP-3 molar ratios ranging from 0.5 to 1.5. More preferably, the molar ratio is 0.9 to 1.3; and most preferably, the product is formulated with approximately a 1:1 molar ratio.

In accordance with the method of the present invention, the IGF and IGFBP-3 are human proteins obtained from natural or recombinant sources. Most preferably, IGF and IGFBP-3 are human IGF-I and IGFBP-3 made by recombinant means and designated rhIGF-I and rhIGFBP-3, respectively. rhIGFBP-3 may be in glycosylated or non-glycosylated form. E. coli is a source of the non-glycosylated rhIGFBP-3. Glycosylated rhIGFBP-3 may be obtained from Chinese hamster ovary (CHO) cells.

The method of the present invention provides for formulating the complex in modes which are readily apparent to those skilled in the art. Preferably, the IGF and IGFBP-3 are complexed prior to administration to the treated individual. Preferably, the complex is formed by mixing approximately equimolar amounts of IGF-I and IGFBP-3 dissolved in physiologically compatible carriers such as normal saline solution or phosphate buffered saline solution. Most preferably, a concentrated solution of rhIGF-I and a concentrated solution of rhIGFBP-3 are mixed together for a sufficient time to form an equimolar complex.

Depending on the mode of administration, compositions of the complex may be in the form of solid, semi-solid or liquid dosage preparations, such as for example, tablets, pills powders capsules, liquids, suspensions or the like. Physiologically compatible carriers include intravenous solutions, such as normal saline, serum albumin, 5% dextrose, plasma preparations, and other protein-containing solutions. The preferred carrier for parenteral administration of the complex is a sterile, isotonic aqueous solution, such as normal saline or 5% dextrose. Alternatively, a solution of the complex may be placed into an implant, such as an osmotic pump, for the slow release of the complex over an extended period of time. Alternatively, the complex may be provided in sustained release carrier formulations such as semipermeable polymer carriers in the form of suppositories or microcapsules. See, for instance, U.S. Pat. No. 3,773,919 for Microcapsular Sustained Release Matrices Including Polylactides; Sidmon et al., (1983) *Biopolymers* 22 (1):547–556 for copolymers of L glutamic acid and γ-ethyl-L-glutamate; Langer et al., (1981) *J. Biomed. Res.* 15:167–277 for poly(2-hydroxyethyl methacrylate) or the like.

The mode of administration delivers the complex to the individual in a safe, physiologically effective manner. The complex may be given by intranasal, subcutaneous, intravenous, intraperitoneal, or other conventional routes of administration. Preferably, the complex is injected subcutaneously, intravenously or intramuscularly. Most preferably, the complex is administered by subcutaneous injection. By subcutaneous injection, the complex appears not to be toxic or mitogenic at the injection site.

The dose of complex to be administered can be readily determined by those skilled in the art, based on the usual patient symptoms discussed above. Preferably, when the complex is administered to humans daily, the dosage of complex is at least about 0.05 mg IGF/kg of body weight/day, complexed to an equimolar amount of IGFBP-3. More preferably, the daily dosage of the complex for humans is at least 0.1 mg IGF/kg/day, complexed to an equimolar amount of IGFBP-3. If daily dosages in excess of about 0.5 mg IGF/kg must be given, the dosage may be divided and injected subcutaneously at two or more sites.

If the IGF/IGFBP-3 complex were administered to humans twice a week, each dose of complex is preferably at least about 0.1 mg IGF/kg of body weight, complexed to an equimolar amount of IGFBP-3. More preferably, for twice weekly administration, the dose of the complex is at least 0.5 mg IGF/kg, complexed to an equimolar amount of IGFBP-3. There is no known upper limit of dosage; however, it is preferable that a single dose not exceed 10 mg IGF/kg of body weight, when the IGF is complexed to an equimolar amount of IGFBP-3. These doses of IGF/IGFBP-3 complex are not expected to cause significant hypoglycemia since IGFBP-3 slows and prolongs the availability of IGF for binding to cellular insulin receptors.

Preferably, the immunodeficient patient is started with a relatively low dose of the complex, such as 0.05 mg IGF/kg of body weight/day. The various factors given above should be monitored to determine if there is improvement. Preferably, the patient would exhibit reduction in fevers, reduced frequency of infections, increase in peripheral blood white count, normalization of clotting function, reversal of skin test anergy, improvement in lymphocyte function tests and increased hematocrit, following such treatment. If the patient improves with the 10 w dose, the 10 w dose preferably should be continued until improvement in general health is achieved. Such an outcome may require several rounds of therapy.

If the patient does not respond to low dose IGF/IGFBP-3 complex with sufficient reversal of the symptoms of the immunodeficiency state, the dose of complex should be increased gradually until such an outcome is achieved.

Another method of the present invention contemplates treating and alleviating conditions in subjects suffering from physiologically excessive levels of IGF-1 that are driving pathologic proliferation of hematogenous tumors or inflammatory diseases by administering a neutralizing or inactivating dose of IGFBP-3 alone.

The formulation, method of administration and dosage will depend upon the disorder to be treated, and the medical history of the patient. These factors are readily determined in the course of therapy. Suitable patients with autoimmune, hyperproliferative or inflammatory disorders can be identified by medical history, physical findings and laboratory tests. The medical history may reveal such facts as adverse reactions to bone marrow or organ transplantation such as graft-versus-host disease. Patients may have physical findings such as rashes, fevers, leukemias, lymphomas, inflammatory bowel disease or psoriasis. Indicative laboratory results include hypergammaglobulinemia, leukocytosis, various coagulopathies, abnormal leukocyte function tests, serum anti-nuclear or other cross-reacting antibodies.

In accordance with the method of the present invention, the formulation comprises IGFBP-3 dissolved in physiologically compatible carriers such as normal saline solution or phosphate buffer saline solution.

Depending on the mode of administration, compositions of the binding protein may be in the form of solid, semi-solid or liquid dosage preparations, such as for example, tablets, pills powders capsules, liquids, suspensions or the like. Physiologically compatible carriers include intravenous solutions, such as normal saline, serum albumin, 5% dextrose, plasma preparations, and other protein-containing solutions. The preferred carrier for parenteral administration of the binding protein is a sterile, isotonic aqueous solution, such as normal saline or 5% dextrose. Alternatively, a solution of the binding protein may be placed into an implant, such as an osmotic pump, for the slow release of the complex over an extended period of time. Alternatively, the binding protein may be provided in sustained release carrier formulations such as semi-permeable polymer carriers in the form of suppositories or microcapsules or topical preparations.

The mode of administration delivers the binding protein to the individual in a safe, physiologically effective manner. The binding protein may be given by intranasal, subcutaneous, intravenous, intraperitoneal, or other conventional routes of administration. Preferably, the binding protein is injected subcutaneously, intravenously or intramuscularly. Most preferably, the binding protein is administered by subcutaneous injection or locally by topical application. By subcutaneous injection, the binding protein appears not to be toxic or mitogenic at the injection site.

The dose of binding protein to be administered can be readily determined by those skilled in the art, based on the usual patient symptoms discussed above. Preferably, when the binding protein is administered to humans daily, the dosage is about 0.5–20 mg/kg of body weight/day. More preferably, the daily dosage of the binding protein for humans is about 2–7 mg/kg/day. The dosage may be divided and injected subcutaneously at two or more sites.

When IGFBP-3 is administered to humans twice a week, each dose is preferably about 2–20 mg/kg of body weight. More preferably, for twice weekly administration, the dose of the binding protein is about 4–8 mg IGFBP-3/kg.

Preferably, the patient with a hematogenous tumor or inflammatory disease driven by IGF is started with a relatively low dose of IGFBP, such as 2 mg of IGFBP-3/kg body weight/day. The various factors given above should be monitored to determine if there is improvement. Preferably, the patient exhibits reduction in fevers, reduced frequency of infections, decrease in peripheral blood white count, normalization of clotting function, improvement in skin lesions, alleviation of symptoms of malabsorption or diarrhea following such treatment. If the patient improves with the low dose, the low dose preferably should be continued until the symptoms of the disorder are reduced, arrested or reversed. Such an outcome may require several rounds of therapy.

If the patient does not respond to low dose IGFBP-3 therapy with sufficient reversal of the symptoms of the disease, the dose of binding protein should be increased gradually until such an outcome is achieved.

The invention has been disclosed by direct description. The following examples are intended to illustrate one embodiment now known for practicing the invention, but the invention is not to be considered limited to these examples.

EXAMPLE I

Effect of IGF-I/IGFBP-3 Complex on Lymphoid Organ Weight and Peripheral Blood Hematologic Response Groups of eight 16-week-old female Sprague-Dawley rats were ovariectomized (OVX) 8 weeks prior to initiation of the study and then treated by subcutaneous injection with various doses of IGF-I, IGF-I/IGFBP-3 or saline vehicle daily for a period of 8 weeks. A sham-operated intact control group of 8 animals was also treated with saline for 8 weeks. Although this study was designed to investigate the effects of several hormone and growth factor preparations on osteopenia, both aging and castration are known to have effects on lymphoid tissue homeostasis and therefore comparisons of the effects of IGF-I/IGFBP-3 on the immune response in treated animals to that seen in both the aged sham and the OVX animals is also relevant. The dosages and treatment conditions utilized are listed below:

Group I: Sham/Saline

Group II: OVX/Saline

Group IX: OVX/0.9 mg/kg IGF-I

Group X: OVX/2.6 mg/kg IGF-I

Group XI: OVX/0.9 mg/kg IGF-I+Equimolar IGFBP-3

Group XII: OVX/2.6 mg/kg IGF-I+Equimolar IGFBP-3

Group XIII: OVX/7.5 mg/kg IGF-I+Equimolar IGFBP-3

(Not shown are data from Groups III–VIII, that were treated with TGF-B2 and estrogen and exhibited no relevant lymphoid tissue effects).

Injection volumes and frequency for all groups were 0.2 ml daily except Group XIII, where the volume was 0.6 ml. Three weeks after initiation of the study, food was withdrawn from the rats at 7 am and betweeen 10 am and noon, and 150 µl of blood was obtained from the tail vein under isoflurane anesthesia. Immediately after the blood sample was collected, each rat received its normal daily injection. A second blood sample was obtained exactly 2 hours later. Plasma glucose levels were measured by a standard colorometric assay involving the oxidation of 0-dianisidine by peroxide produced by the plasma glucose as a result of treatment with glucose oxidase. Animals were sacrificed after 8 weeks of treatment by exsanguination under ketamine/xylazine anesthesia. Blood samples were subjected to routine hematologic and clinical chemistry analyses. Full necropsies and histopathologic examinations of soft and calcified tissues were performed.

Table 1 shows the effect of two doses of IGF-I alone or equivalent and higher doses of IGF-I delivered in complex with IGFBP-3 on thymic weight as a percentage of total body weight. A two-factor ANOVA statistical test indicated that there was a significant effect of dose (P<0.01) on thymus weight and some advantage (P=0.09) of combining IGFBP-3 with IGF-I as compared to IGF-I treatment. The highest dose of IGF-I/IGFBP-3 doubled the normalized thymus weight. The same dose of IGF-I alone could not be given without severe and probably lethal hypoglycemia. See FIG. 1. Histologic examination of the thymus from IGF-I/IGFBP-3-treated animals revealed normal morphology and a normal cortical/medullary ratio.

TABLE 1

| Group | Normalized Organ Weight Data | | | | |
|---|---|---|---|---|---|
| | Thymus | Spleen | Liver | Kidneys | Gastrocnemius |
| Sham + Saline | 0.67 ± 0.05 | 1.8 ± 0.1 | 26.2 ± 1.0 | 6.4 ± 0.2 | 4.7 ± 0.1 |
| OVX + Saline | 0.73 ± 0.05 | 1.7 ± 0.1 | 21.6 ± 0.7* | 5.3 ± 0.1* | 4.5 ± 0.2 |
| 0.9 mg/kg rhIGF-I | 1.04 ± 0.06 | 1.8 ± 0.2 | 21.0 ± 0.4 | 6.4 ± 0.2 | 4.5 ± 0.1 |
| 2.6 mg/kg rhIGF-I | 0.89 ± 0.05 | 2.0 ± 0.1 | 21.3 ± 0.4 | 5.4 ± 0.2 | 4.7 ± 0.2 |
| 0.9 mg/kg rhIGF-I:IGFBP-3 | 1.21 ± 0.12 | 1.7 ± 0.1 | 21.9 ± 0.8 | 5.7 ± 0.1 | 4.5 ± 0.2 |
| 2.6 mg/kg rhIGF-I:IGFBP-3 | 1.07 ± 0.12 | 2.1 ± 0.1 | 21.4 ± 0.7 | 5.6 ± 0.1 | 4.3 ± 0.1 |
| 7.5 mg/kg rhIGF-I:IGFBP-3 | 1.49 ± 0.13 | 2.3 ± 0.1 | 21.3 ± 0.7 | 5.9 ± 0.2 | 4.2 ± 0.1 |
| ANOVA P Value (Dose) | <0.01 | <0.001 | 0.91 | 0.58 | 0.66 |
| ANOVA P Value (Treatment) | 0.09 | 0.98 | 0.49 | 0.16 | 0.34 |

Data are expressed in terms of grams/kg body weight and are presented as means ± SEM. All rats treated with rhIGF-I or rhIGF-I/IGFPB-3 were OVX. A two-factor ANOVA was performed to determine the effects of dose (rhIGF-I and rhIGF-I/IGFBP-3 groups) and treatment (rhIGF-I versus rhIGF-I/IGFBP-3).
*Significantly different from Sham at P < 0.01 by Student's t-test.

Figure 2:
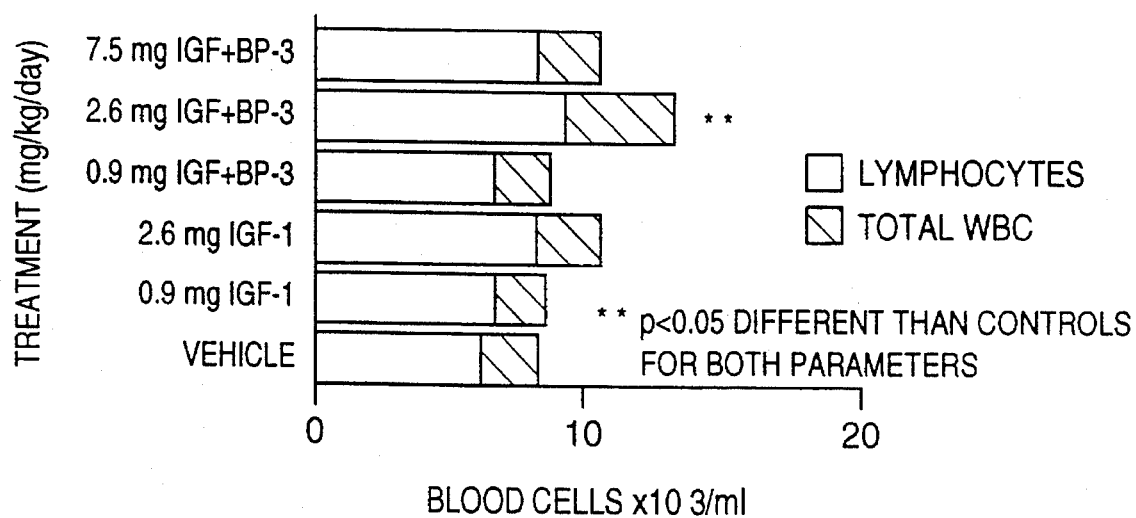
FIG. 2 graphically shows peripheral white blood cell counts.

FIG. 2 shows the effect of these same treatment regimens on peripheral blood white blood cell (WBC) numbers. Some increase in WBCs was achieved after 8 weeks of administration of the highest dose of free IGF-I (2.6 mg/kg/day). However, a more pronounced and significant (p=0.0045) response was induced by treatment with the equivalent dose of IGF-I delivered as a complex with IGFBP-3.

This peripheral WBC increase was mostly due to an increase in the lymphocyte population, with little change in the numbers of neutrophils, monocytes or eosinophils. A dose of IGF-I/IGFBP-3 complex greater than 2.6 mg/kg/day did not increase the peripheral blood WBC response. These findings indicate that IGF-I/IGFBP-3 treatment accelerated maturational events in the lymphoid tissues, most probably within the thymus, that result in an increase in the export of normal-appearing, presumably functional T-cells to the peripheral circulation. It is highly likely that these lymphocytes can contribute to an increased immune response desirable under conditions of immunosuppression or infection.

EXAMPLE II

Method of Assessing Effect of IGF-I/IGFBP-3 on Erythropoiesis

The response of the red cell compartment to IGF-I/IGFBP-3 was also assessed in the experiment described in Example I. There was a significant 6±0.5% increase in total hemoglobin (p=0.006) produced by treatment with 7.5 mg/kg/day IGF-I/IGFBP-3 but no statistically significant changes in hematocrit, erythrocyte number or mean corpuscular volume were observed. This contrasts with the finding of Kurtz et al. (1988), supra, that treatment of hypophysectomized rats with IGF-I alone caused no change in hematocrit but increased the blood level of erythropoietin.

The above demonstrated increases in efficacy of the immunohematopoietic response achieved by administration of IGF-I/IGFBP-3 indicate that this therapy can stimulate at least one facet of erythropoiesis, perhaps most usefully in patients suffering from anemia associated with chronic renal failure. For further information about the anemia of chronic renal failure, see Urena, P., et al. (1992) Nephrol. Dial. Transplant. 7:40–44.

EXAMPLE III

Effect of IGF-I/IGFBP-3 Complex and IGFBP-3 Alone on Lymphoid Organ Weights

Groups of 10 male Sprague-Dawley rats were hypophysectomized (HYPOX) approximately two weeks prior to the initiation of the study and then were treated by subcutaneous injection with various doses of IGF-I, IGF-I/IGFBP-3 or IGFBP-3 alone or the saline vehicle twice daily for eight days. Although this study was designed to investigate the effects of several hormone and growth factor preparations on general weight gain and lean body mass, hypophysectomy is also known to affect lymphoid tissue homeostasis. Therefore, comparisons of the effects of IGF-I/IGFBP-3 on the immune organ weights in treated animals with that seen in the HYPOX controls is also relevant. The dosages and treatment conditions utilized are listed below:

Group I: HYPOX/saline

Group IV: HYPOX/30 μg IGF-I

Group V: HYPOX/150 μg IGF-I

Group VI: HYPOX/120 μg IGFBP-3 alone

Group VII: HYPOX/600 μg IGFBP-3 alone

Group VIII: HYPOX/30 μg IGF-I+120 μg IGFBP-3

Group IX: HYPOX/120 μg IGF-I+600 μg IGFBP-3

Not shown are data from Groups II and III, because they were treated with growth hormone alone and exhibited no relevant lymphoid tissue effects.

The total dosages above are stated in terms of treatment per rat/day and were delivered in two equal injection volumes of 0.2 ml each administered approximately 11 hours apart. The range of onset body weights for all groups of rats was 55.8–64.9 g. At the conclusion of the experiment, after the collection of blood under anesthesia, the animals were sacrificed by cervical dislocation. Selected organs were obtained for wet tissue weight determinations.

Figure 3:
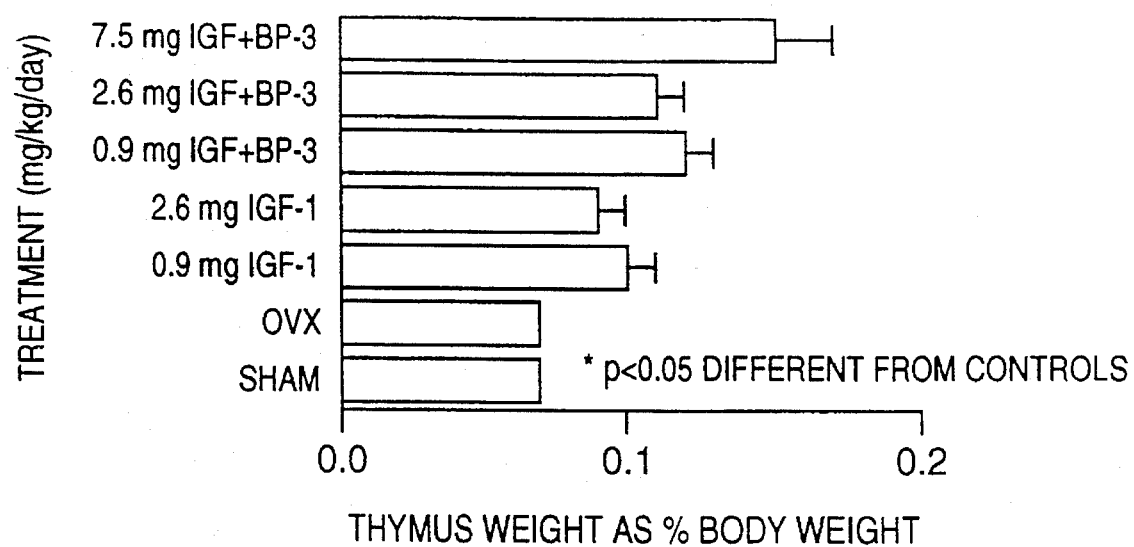
FIG. 3 graphically presents thymic weights.

FIG. 3 shows the effect of treatment with two doses of IGF-I/IGFBP-3 complex or equivalent doses of IGFBP-3 alone on thymic weight as a percentage of total body weight. Half of the rats treated with 150 μg of free IGF-I died on this treatment. Although not verified by blood glucose concentrations, the cause of death was probably acute hypoglycemic shock, which is a well known consequence of bolus administration of large dosages of free IGF-I. All rats receiving an equivalent dosage of IGF-I complexed to IGFBP-3 survived the experiment, confirming the increased safety margin achieved by administration of IGF-I in complex with IGFBP-3 as described in Sommer et al. (1991), supra.

The mean thymic weight as a percentage of total body weight increased during IGF-I/IGFBP-3 treatment compared to saline-treated controls. However, this change was not statistically significant. Treatment with 600 μg/rat of IGFBP-3 alone decreased the mean thymic weight as a percentage of total body weight compared to controls. While the difference after only eight days of treatment did not reach statistical significance, it is likely that longer administration of IGFBP-3 alone (beyond the eight-day period) would have yielded significant changes in the lymphoid tissue response. Thus, the combination of IGF and IGFBP appeared to be somewhat beneficial in hypophysectomized rats which have low levels of IGF.

These findings suggest that IGF binding proteins, particularly IGFBP-3, can be used systemically to antagonize IGF-I-driven lymphoproliferative events such as seen in leukemias or inflammatory skin diseases, even though IGF is in relatively normal concentrations.

This invention has been detailed both by example and by direct description. It should be apparent that one having ordinary skill in the art would be able to surmise equivalents to the invention as described in the claims which follow but which would be within the spirit of the description above. Those equivalents are to be included within the scope of this invention.

We claim:

1. A method of treating a subject with an anemia characterized by deficient total hemoglobin, said method comprising administering to the subject a complex comprising insulin like growth factor-1 (IGF-1) and insulin-like growth factor binding protein-3 (IGFBP-3) in a ratio of IGF-1:IGFBP-3 from 0.5 to 1.5 and in an amount sufficient to improve the level of total hemoglobin.

* * * * *